US012011222B2

(12) United States Patent
Bower et al.

(10) Patent No.: US 12,011,222 B2
(45) Date of Patent: Jun. 18, 2024

(54) INTERLOCK TO DEFINE A FIXED SPATIAL RELATIONSHIP BETWEEN MEDICAL INSTRUMENTS

(71) Applicant: Avenda Health, Inc., Santa Monica, CA (US)

(72) Inventors: Stephen Bower, Morgan Hill, CA (US); Benjamin Scott Arnett, Hollister, CA (US); Shyam Natarajan, Santa Monica, CA (US); Gary Hulme, San Jose, CA (US)

(73) Assignee: AVENDA HEALTH, INC., Santa Monica, CA (US)

( * ) Notice: Subject to any disclaimer, the term of this patent is extended or adjusted under 35 U.S.C. 154(b) by 1052 days.

(21) Appl. No.: 16/866,272

(22) Filed: May 4, 2020

(65) Prior Publication Data

US 2020/0345419 A1 Nov. 5, 2020

Related U.S. Application Data

(60) Provisional application No. 62/842,248, filed on May 2, 2019.

(51) Int. Cl.
*A61B 18/22* (2006.01)
*A61B 18/00* (2006.01)
*A61B 18/20* (2006.01)

(52) U.S. Cl.
CPC .... *A61B 18/22* (2013.01); *A61B 2018/00172* (2013.01); *A61B 2018/00577* (2013.01);
(Continued)

(58) Field of Classification Search
CPC ......... A61B 18/22; A61B 2018/00172; A61B 2018/00577; A61B 2018/00791;
(Continued)

(56) References Cited

U.S. PATENT DOCUMENTS

| 5,242,438 A | 9/1993 | Saadatmanesh et al. |
| 5,292,320 A | 3/1994 | Brown et al. |

(Continued)

FOREIGN PATENT DOCUMENTS

| EP | 1379313 B1 | 2/2006 |
| EP | 1647305 B1 | 12/2010 |

(Continued)

*Primary Examiner* — Amber R Stiles
(74) *Attorney, Agent, or Firm* — Dorsey & Whitney LLP

(57) ABSTRACT

A system for fixing a spatial relationship between medical instruments can include an interlock component including a body defining an aperture to receive and retain a first needle, a head connected to the body and defining a slot extending parallel to the aperture, and a first magnet at least partially surrounded by the head and disposed between the aperture and the slot. The system can also include a handle to receive and retain a second needle, the handle defining a retaining feature for receiving a portion of the interlock component and including a second magnet positioned adjacent to the retaining feature. The second magnet attracts the first magnet to retain the portion of the interlock component in the retaining feature such that the interlock component is oriented in a desired spatial relationship relative to the handle.

14 Claims, 9 Drawing Sheets

(52) U.S. Cl.
CPC .............. *A61B 2018/00791* (2013.01); *A61B 2018/0091* (2013.01); *A61B 2018/2005* (2013.01); *A61B 2018/225* (2013.01); *A61B 2560/0214* (2013.01); *A61B 2562/0238* (2013.01); *A61B 2562/0271* (2013.01)

(58) Field of Classification Search
CPC .... A61B 2018/0091; A61B 2018/2005; A61B 2018/225; A61B 2560/0214; A61B 2562/0238; A61B 2562/0271; A61B 90/11; A61B 90/50; A61B 2017/00477
See application file for complete search history.

(56) References Cited

U.S. PATENT DOCUMENTS

| | | |
|---|---|---|
| 6,450,962 B1 | 9/2002 | Brandl et al. |
| 6,544,257 B2 | 4/2003 | Nagase et al. |
| 6,802,838 B2 | 10/2004 | Loeb et al. |
| 7,270,656 B2 | 9/2007 | Gowda et al. |
| 8,175,350 B2 | 5/2012 | Suri et al. |
| 8,211,095 B2 | 7/2012 | Gowda et al. |
| 8,425,418 B2 | 4/2013 | Suri et al. |
| 8,523,847 B2 | 9/2013 | Dewey et al. |
| 8,696,654 B2 | 4/2014 | Mihajlovic et al. |
| 8,851,080 B2 | 10/2014 | Gowda et al. |
| 9,339,336 B2 | 5/2016 | Gowda et al. |
| 9,398,930 B2 | 7/2016 | Leung et al. |
| 9,693,826 B2 | 7/2017 | Neuberger |
| 9,700,342 B2 | 7/2017 | Andrews et al. |
| 2004/0034297 A1 | 2/2004 | Darrow et al. |
| 2014/0107642 A1* | 4/2014 | Rios .................. A61B 17/3478 606/41 |
| 2019/0029756 A1* | 1/2019 | Natarajan .............. A61B 18/20 |

FOREIGN PATENT DOCUMENTS

| | | |
|---|---|---|
| EP | 1909679 B1 | 11/2013 |
| EP | 2799111 A1 | 11/2014 |
| EP | 2677937 B1 | 4/2020 |
| JP | 2005312950 A | 11/2005 |
| WO | 2017132345 A1 | 8/2017 |

* cited by examiner

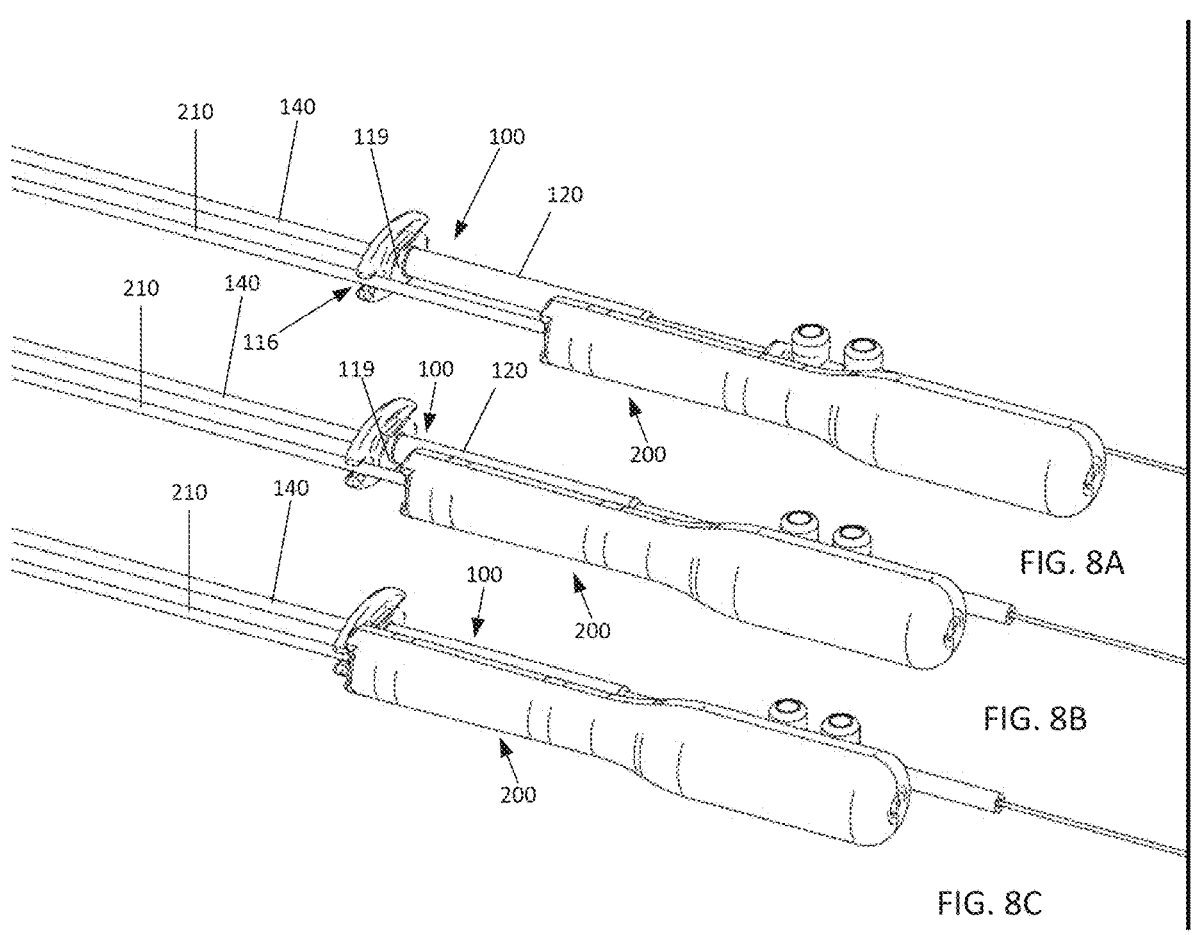

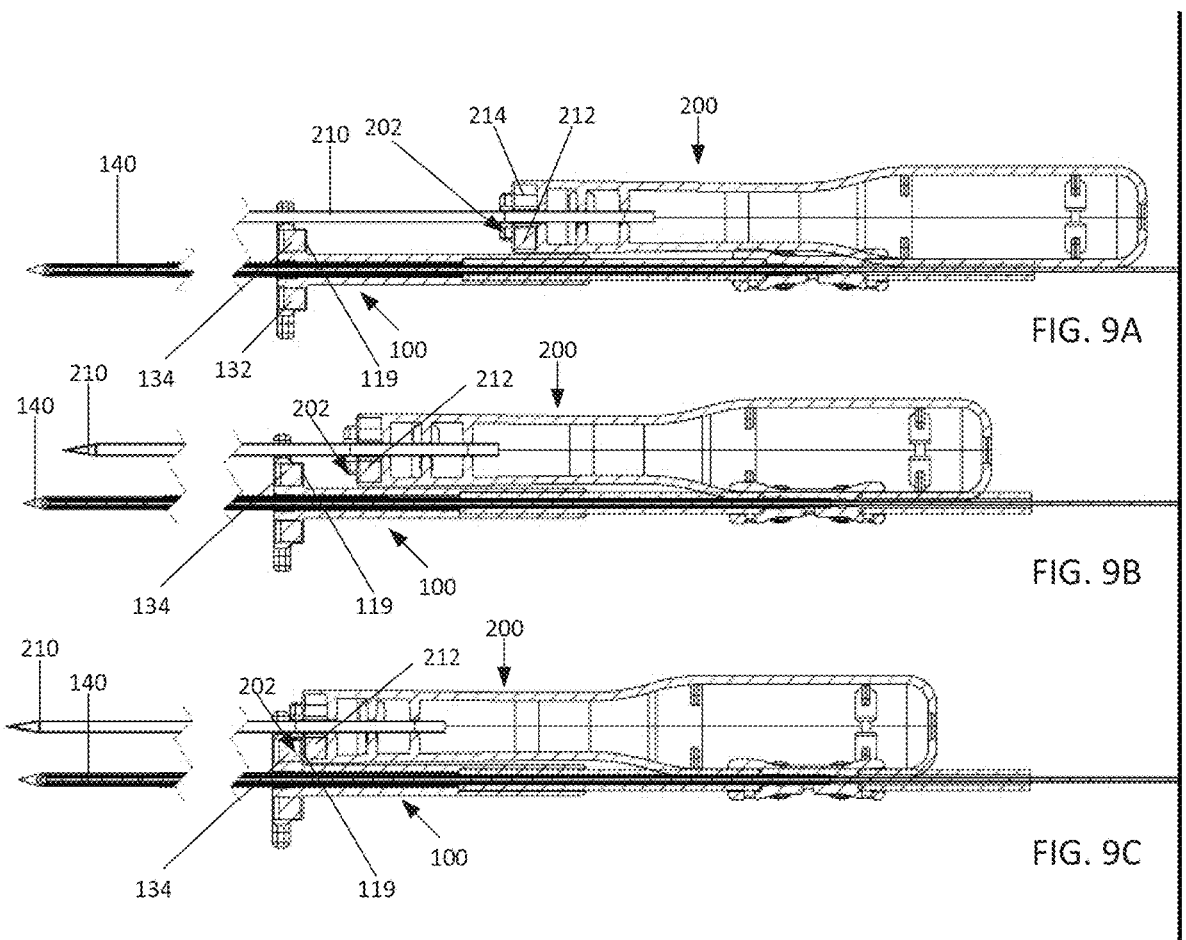

INTERLOCK TO DEFINE A FIXED SPATIAL RELATIONSHIP BETWEEN MEDICAL INSTRUMENTS

CROSS REFERENCE TO RELATED APPLICATIONS

The present application claims the benefit of U.S. Provisional Application No. 62/842,248 filed on May 2, 2019, titled "Interlock to Define a Fixed Spatial Relationship Between Medical Instruments," the disclosure of which is incorporated herein, by reference in its entirety.

FIELD

The present disclosure relates generally to medical devices. More particularly, the present disclosure relates to medical devices used in interstitial therapies and treatments.

BACKGROUND

A challenge with real-time monitoring of interstitial therapies, such as ablative therapies, is that the angle and position of a sensor monitoring an interstitial energy source relative to that energy source must be known to provide accurate data. When using point source sensors, these relative positions can be used to reconstruct the effects of the energy source being monitored. For example, in laser ablation, point temperature sensors can be used to estimate the temperature at arbitrary points between such sensors, providing an improved guide for a physician.

SUMMARY

A system for fixing a desired spatial relationship between medical devices can include an interlock component having a body defining an aperture to receive and retain a first needle, a head connected to the body and defining a slot extending parallel to the aperture, a first magnet at least partially surrounded by the head disposed between the aperture and the slot, and a handle to receive and retain a second needle, the handle defining a retaining feature for receiving a portion of the interlock component and including a second magnet positioned adjacent to the retaining feature, wherein the second magnet attracts the first magnet to retain the portion of the interlock component in the retaining feature such that the interlock component is oriented in the desired spatial relationship relative to the handle.

According to some aspects, the system can further include a first needle retained by the body and a second needle retained by the handle. The desired spatial relationship between the interlock component and the handle can correspond to a desired spatial relationship between the first needle and the second needle. The first needle can include a thermal sensor, an optical sensor, or a multimodal sensor. The second needle can include an energy source. The first and second magnets can include rare-earth magnets. The body and head can include polycarbonate. A thickness of material between the first magnet and a rear surface of the head can be less than about 0.01 inches. The handle can include a protrusion disposed opposite the retaining feature to prevent retention of the interlock component by the handle in an undesired spatial relationship. The handle can include a third magnet to exert a repulsive force on the first magnet when the interlock component is not oriented in the desired spatial relationship relative to the handle. The interlock component can be rotatable with respect to the handle when the second needle is disposed in the slot, and the portion of the interlock component is not received by the retaining feature. The desired spatial relationship can include a desired angle and spatial offset between the interlock component and the handle. The system can provide a visible indicia that the interlock component and handle are in the desired spatial relationship. The portion of the interlock component can include a protrusion and the retaining feature can include a portion of the handle defining a slot having a size and shape corresponding to the protrusion.

A system for fixing a desired spatial relationship between medical devices can include an interlock component having a body and a first needle extending from the body, a head connected to the body and defining a slot extending parallel to the first needle to receive a second needle, and a protrusion extending from the head adjacent to the body, a handle defining a retaining feature sized to receive and engage the protrusion when the interlock component is disposed in the desired spatial orientation relative to the handle, the second needle extending from the handle, and a coupling mechanism to retain the interlock component against the handle when the interlock component is in the desired spatial relationship relative to the handle.

According to some aspects, the coupling mechanism can include a first magnet affixed to the interlock component and a second magnet affixed to the handle and the first and second magnets can exert an attractive force on one another to retain the interlock component against the handle when the interlock component is in the desired spatial relationship relative to the handle.

A method of fixing a spatial relationship between two needles can include positioning a slot defined by an interlock component surrounding a first needle at least partially around a second needle, positioning the interlock component adjacent to a handle of the second needle so that a portion of the interlock component engages a corresponding retaining feature of the handle to retain the interlock component in a desired spatial relationship with the handle, securing the interlock component to the handle in the desired spatial relationship by an engagement between a portion of the interlock component and a portion of the handle, and providing a visible indicia when the interlock component and the handle are in the desired spatial relationship.

According to some aspects, the engagement can include at least one of a magnetic engagement, a mechanical engagement, and an electromechanical engagement. The desired spatial relationship can include a desired angle and spatial offset between the interlock component and the handle. The desired spatial relationship between the interlock component and the handle can correspond to a desired spatial relationship between the first need and the second needle.

BRIEF DESCRIPTION OF THE DRAWINGS

The disclosure will be readily understood by the following detailed description in conjunction with the accompanying drawings, wherein like reference numerals designate like structural elements, and in which:

FIG. 8A-C shows a perspective view of an interlock component mating with a handle.

FIG. 9A-C shows a cross-sectional top view of an interlock component mating with a handle.

DETAILED DESCRIPTION

Figure 1:
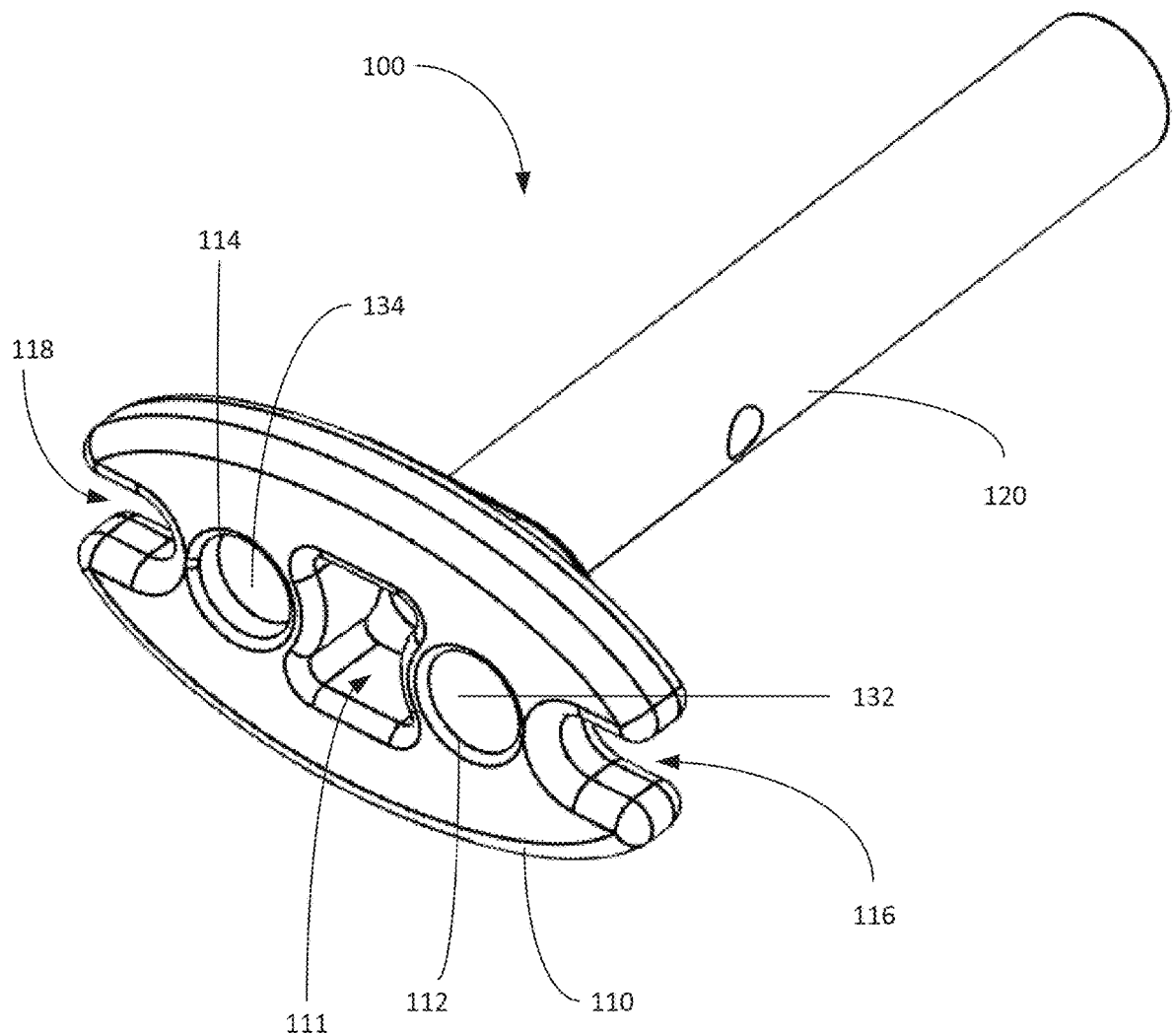
FIG. 1 shows a perspective view of an interlock component.

The present description provides examples, and is not limiting of the scope, applicability, or configuration set forth in the claims. Thus, it will be understood that changes can be made in the function and arrangement of elements discussed, without departing from the spirit and scope of the disclosure, and various embodiments can omit, substitute, or add other procedures or components as appropriate. For instance, methods described can be performed in an order different from that described, and various steps can be added, omitted, or combined. Also, features described with respect to some embodiments can be combined in other embodiments.

Various medical treatments, therapies, and procedures, for example, interstitial or minimally invasive therapies, can require the use of two or more medical instruments that can be inserted into the body of a patient. In many cases, in order to accurately and successfully perform such a therapy, the spatial relationship between the medical instruments or devices, as well as their position in the body, may be monitored and maintained in a desired arrangement.

For example, in a focal laser ablation (FLA) or laser interstitial thermal therapy (LITT) procedure carried out to treat prostate cancer an interstitial energy source, such as a laser fiber, is inserted into a desired location of the patient's prostate and thermal energy is delivered to the location to induce coagulation necrosis of cancerous prostate tissue. As the goal is to induce necrosis of cancerous tissue while causing minimal damage to adjacent tissue, the position, duration, and amount of energy delivered by the interstitial energy source is closely monitored. This monitoring can be achieved by a sensor or sensors, such as a photovoltage fiber, that are also interstitially provided to a desired location in the patient's body close to the energy source. In order to accurately monitor the energy source, for example, as part of determining the degree of ablation or necrosis that has occurred during the procedure, a desired spatial relationship between the energy source and the sensor or sensors may be maintained during monitoring. In some examples, this desired spatial relationship can include a desired spatial offset and angle between the energy source and sensor. In some other examples, the desired spatial relationship can include a range of spatial offsets or angles between the two devices or instruments. As the spatial relationship between the energy source and sensor are known and fixed, accurate measurements can thus be achieved during treatment.

A system to fix, retain, or otherwise maintain a desired spatial relationship between two medical instruments, such as needles or devices used in interstitial therapy, can include a handle and an interlock component. The handle and interlock component can each receive, retain, be attached or affixed to, or otherwise include at least one needle. The handle and interlock component can be selectively coupled to one another, for example, by a coupling mechanism or system, in a desired spatial relationship. As the interlock component and handle each retain at least one needle, the needles are likewise maintained in a corresponding desired spatial relationship, for example, as may be desired for use in an interstitial therapy.

The term needle is used broadly herein to refer to any medical device or instrument that is insertable into the body of a patient. For example, the term needle can be used to refer to a needle, catheter, trocar, fiber, such as a laser or optical fiber, sensor, such as an optical, thermal, or multi-modal sensor, hypotube, and the like. Similarly, the terms spatial relationship and spatial offset are used broadly herein to describe the relative spatial positions of two or more bodies. The term spatial relationship can include the spatial offset, or physical separation between the two bodies as measured in one, two, or three dimensions, as well as the angle of each body relative to one another, again measured in any number of dimensions. For example, a desired spatial offset between two devices can be described as a lateral distance between the two devices as well as a proximal or distal difference between the position of each device relative to the body of the patient.

In some examples, the desired spatial relationship between the handle and the interlock component of a system described herein can be achieved and maintained by a coupling system or mechanism. The coupling system can include or be provided by portions of the handle and the interlock component. For example, the interlock component can have an engagement feature and the handle can have a corresponding retention feature. In use, the engagement feature can engage with, and be received by, the retention feature to selectively fix the spatial relationship between the interlock component and handle. In some examples, the coupling system or mechanism can include a magnetic engagement, a mechanical engagement, such as a clip or snap-fit, an electromechanical engagement, or combinations thereof between the interlock component and the handle.

The system can also provide a visual indication to a user that the desired spatial relationship between the interlock component and the handle, and thus the two or more needles, has been achieved. In some examples, if the interlock component and the handle are not aligned in the desired spatial relationship, then a gap between the two components may be visible. In some examples, certain portions of the interlock component and/or handle can be colored such that the colored portion is readily visible when the components are not in the desired spatial relationship and the colored portion is not visible when the components are in the desired spatial relationship. Other visual indicia of alignment in the desired spatial relationship can also be provided by the system, for example, with LEDs, moveable components, and the like.

These and other embodiments are discussed below with reference to FIGS. 1-9C. However, those skilled in the art will readily appreciate that the detailed description given herein with respect to these Figures is for explanatory purposes only, and should not be construed as limiting.

FIG. 1 shows an example of an interlock component 100 that can be part of a system for fixing a desired spatial relationship between medical devices or instruments, as described herein. In some examples, the interlock component 100 can include a body 120 that can define an aperture 111 for receiving and retaining a needle (not shown). The aperture 111 can be sized to correspond to a diameter of a needle, and the body 120 can further include features to retain the needle in a fixed position within the aperture 111, as described herein.

The interlock component 100 can also include a head 110 that can at least partially define the aperture 111, and that can be joined with the body 120. In some examples, the body 120 and the head 110 can be integrally formed, although in some examples, the body 120 and head 110, as well as other portions of the interlock component 100, can be formed separately and joined together, for example, via an adhesive, mechanical engagement, and the like.

The head 110 is illustrated as having a substantially ovoid shape, although in some examples, the head 110 can be any desired shape. A portion of the head 110 can extend past the width of the body 120 to define at least one slot 116 sized to receive a second needle, for example, a needle associated with a handle of the system, as described further herein. In some examples, the portion of the head defining the slot 116 can have a U-shape, although the portion can define a slot having substantially any desired shape to receive a second needle, as described herein. Further, in some examples, the slot 116 can be an aperture or through-hole that is fully encompassed and defined by a portion of the head 111.

In some examples, and as shown in FIG. 1, the head 110 can include a portion that defines a second slot 118. In some cases, the second slot 118 can have the same size and shape as the slot 116, although in some examples the slot 118 can have substantially any desired size and shape. The slot 118 can similarly be sized to receive a second needle, for example, a second needle associated with a handle of the system, as described herein. In some cases, the slot 118 can be positioned directly opposite the slot 116 so that the head 110 is rotationally symmetrical. This configuration can allow for greater ease of use, for example, by allowing either slot 116 or slot 118 to receive the second needle, as described herein. Although the head 110 of the interlock component 100 is illustrated as defining two slots 116, 118, in some examples, the head 110 can define any number of slots as desired.

The head 110 can further define at least one cavity 112 for receiving a magnet 132 therein. In some examples, the head 110 can define a second cavity 114 for receiving a second magnet 134. In some examples, the cavities 112, 114 can be substantially the same size and shape, and the magnets 132, 134 can similarly be the same size and shape. In some examples, a cavity 112 can be positioned adjacent to the aperture 111. In some examples, a cavity 112 can also be positioned adjacent to a slot, such as slot 116, so that a magnet 132 disposed in the cavity 112 can be positioned between the aperture 111 and the slot 116.

A magnet 132, 134 can have substantially any desired shape and size, although in some cases the magnets 132, 134 can be cylindrical. Further, the magnets 132, 134 can be any form of magnet, such as permanent magnets, electromagnets, and the like. In some examples, the magnets 132, 134 can be rare-earth magnets, such as neodymium sintered magnets. A magnet, such as magnet 132, can be substantially completely surrounded by the head 110 such that no magnetic material is exposed to the ambient environment outside of the head 110. In some examples, a magnet 132, 134 can thus be incorporated into the head 110 during a molding or casting process. For example, in some cases where the head includes a polymeric material, a magnet 132, 134 can be incorporated into the head 110 during a single shot or multi-shot injection molding process. In some other examples, the head 110 can be formed with a cavity 112, 114, and a magnet 132, 134 can be inserted into the cavity 112, 114 and additional material can be provided to enclose the magnet 132, 134 in the cavity 112, 114.

The interlock component 100, including the head 110 and/or body 120 can be formed from or include a polymeric material. In some examples, the interlock component can be formed from polycarbonate, although in some cases, substantially any polymeric material capable of withstanding sterilization in an autoclave can be used.

Figure 2:
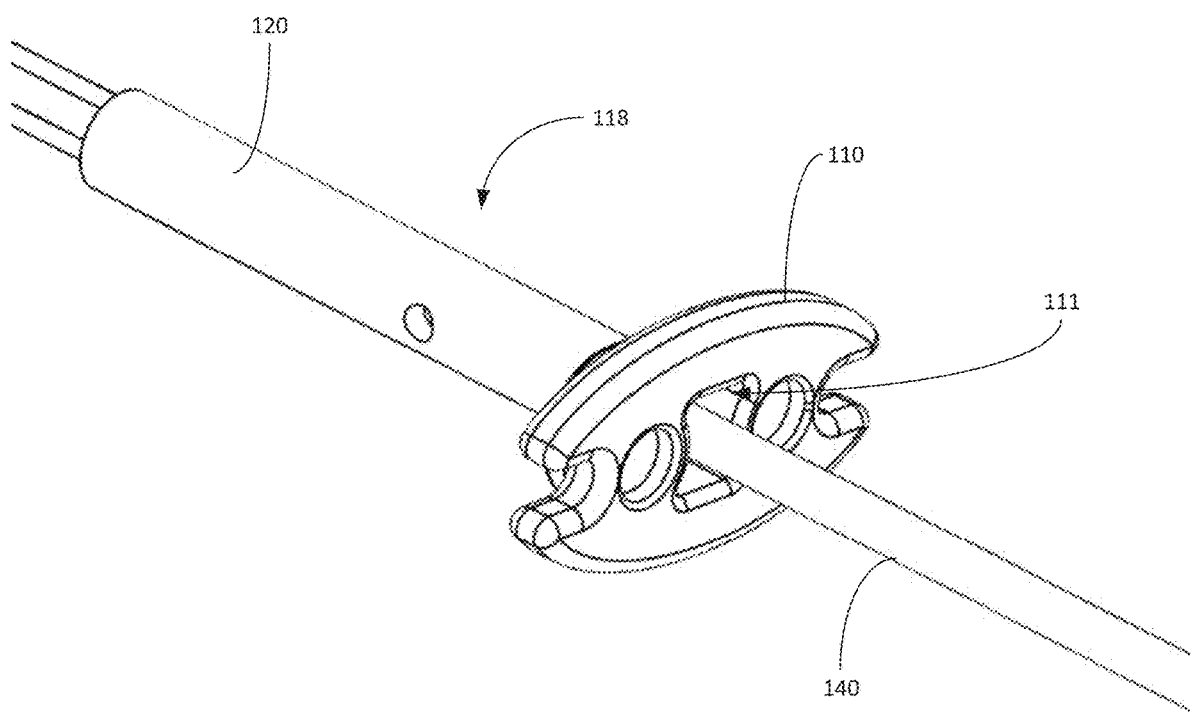
FIG. 2 shows a front perspective view of an interlock component and a needle.

FIG. 2 shows an example of the interlock component 100 including a needle 140 passing through the aperture 111 defined by the head 110 and the body 120 of the interlock component 100. The needle 140 is fixed in this position and maintained in the aperture 111 of the interlock component. The needle 140 can be maintained in this position relative to the interlock component 100 by features of the interlock component 100, additional retention components or mechanisms, or because the needle is integrally formed or adhered to some portion of the interlock component 100. In some examples, by retaining the needle 140 in the aperture 111 of the interlock component 100, fixing the spatial relationship between the interlock component 100 and another component of the system, such as the handle, can thus fix the spatial relationship of the needle 140 with respect to other components, such as a second needle, as described herein.

Figure 3:
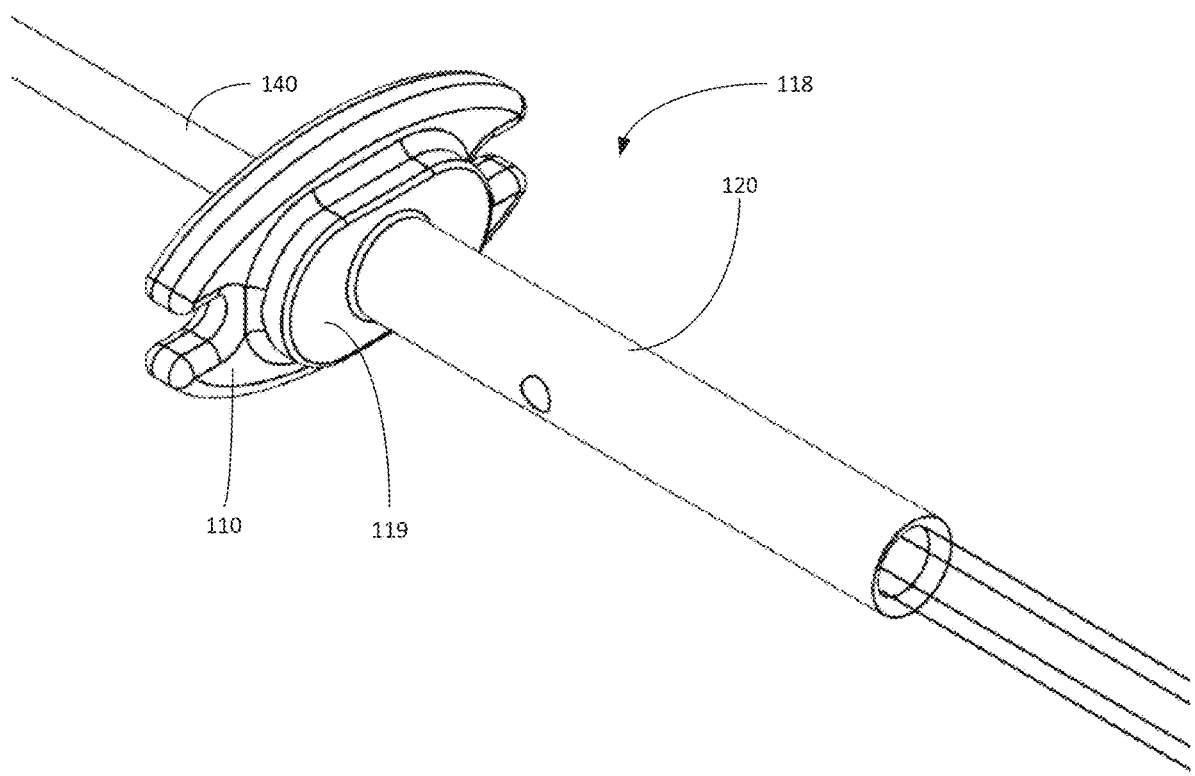
FIG. 3 shows a rear perspective view of an interlock component and a needle.

FIG. 3 shows a rear perspective view of the interlock component 100 including the needle 140 passing through aperture 111 and fixed in position. As can be seen, the head 110 of the interlock component 100 can include an engagement feature or portion, for example, a protrusion 119. In some examples, the protrusion 119 can extend from a surface of the head 110 adjacent to the body 120. In some examples, the protrusion 119 can be positioned adjacent to the location that the body 120 meets the head 110. In some examples, and as illustrated, the protrusion 119 can surround the location that the body 120 meets the head, and further, the body 120 can meet, abut, or extend from the protrusion 119. As described further herein, in some examples, the protrusion 119 can be an engagement feature that is engaged with or is received by a corresponding feature of another component of the system, for example, a handle, to aid in fixing the spatial relationship of the components.

Figure 4:
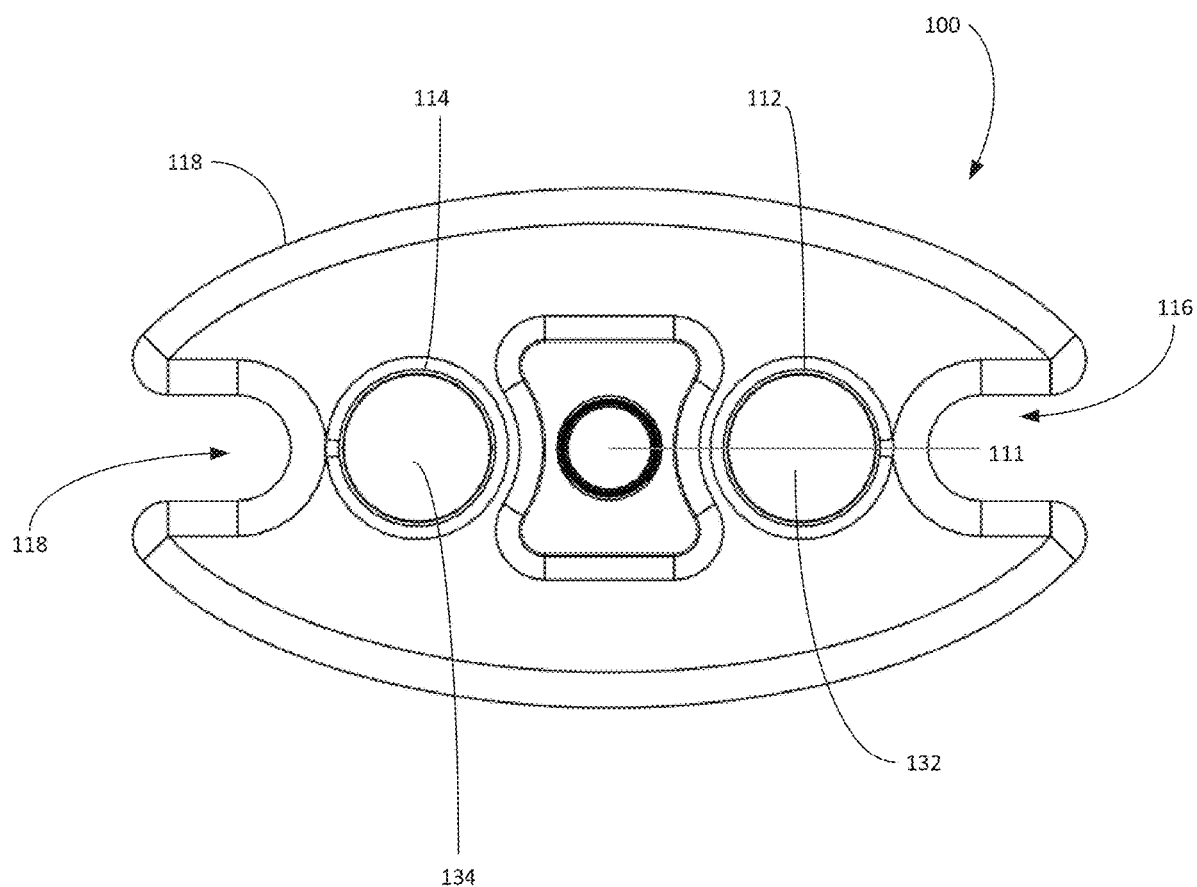
FIG. 4 shows a front view of an interlock component.

FIG. 4 shows a front view of the interlock component 100 including the head 110, the aperture 111, and the slots 116, 118. The positions of the cavities 112, 114 and magnets 132, 134 that are disposed therein are also shown. As can be seen, each of the magnets 132, 134 is disposed between a corresponding slot 116, 118, and the central aperture 111 is defined by the interlock component. In some cases, the offset between a slot 116, 118 and the aperture 111 can be less than 10 mm, for example, about 8 mm, and can correspond to a desired spatial offset between the needle disposed in the aperture 111 and a second needle received by the slot 116, 118. Accordingly, in some examples, a magnet 132, 134 can be sized to fit in the space between a slot 116, 118 and the aperture 111.

Figure 5:
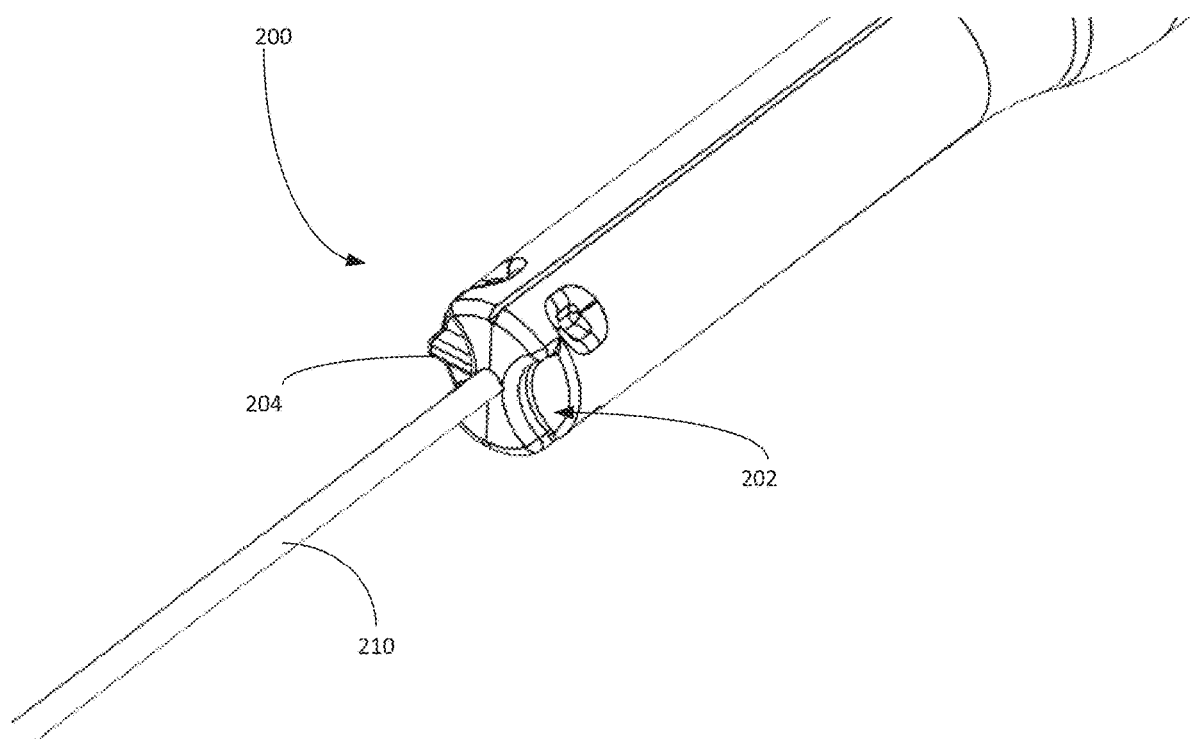
FIG. 5 shows a front perspective view of a handle including a needle.

FIG. 5 shows a front perspective view of a portion of a handle 200, including a needle 210 affixed to the handle 200 that can be part of a system for fixing a desired spatial relationship between medical devices or instruments, as described herein, and that can include the interlock component 100 described with respect to FIGS. 1-4.

In some examples, the needle 210 can be a laser fiber or laser catheter and the handle 200 can be a handle used in the operation of the needle 210. The proximal, or patient-facing portion of the handle 200 is shown in FIG. 5, and the handle can include additional features or components that are not illustrated. The proximal portion of the handle 200 can define a retaining feature 202 that can be in the form of a slot or a cut-out. In some examples, the retaining feature 202 can be sized to correspond to the protrusion 119 of the interlock component 100, as described herein. The retaining feature 202 can be positioned adjacent to where the needle 210 meets or enters the handle 200, although in some examples, the retaining features 202 can be offset from the needle 210 by a desired distance. The handle can also include a magnet (not shown) positioned internally and adjacent to a surface of the retaining feature 202. The magnet can align with and exert an attractive force on a magnet 132, 134 of the interlock component, as described herein.

In some examples, the handle 200 can also include a feature, such as rib 204, positioned opposite or opposing the retaining feature 202 on a proximal end of the handle 200 that can prevent or inhibit engagement of the engagement feature or protrusion 119 of the interlock component 100 with the handle 200 when the handle 200 and interlock component 100 are not arranged in a desired spatial relationship, as described further herein. Additionally, a second magnet (not shown) can be positioned internally in the handle 200 and adjacent to the feature or rib 204. This second magnet can exert a repulsive force on a magnet 132, 134 of the interlock component if the interlock component 100 is moved towards the handle 200 and is not in a desired spatial relationship therewith, as described herein.

Figure 6:
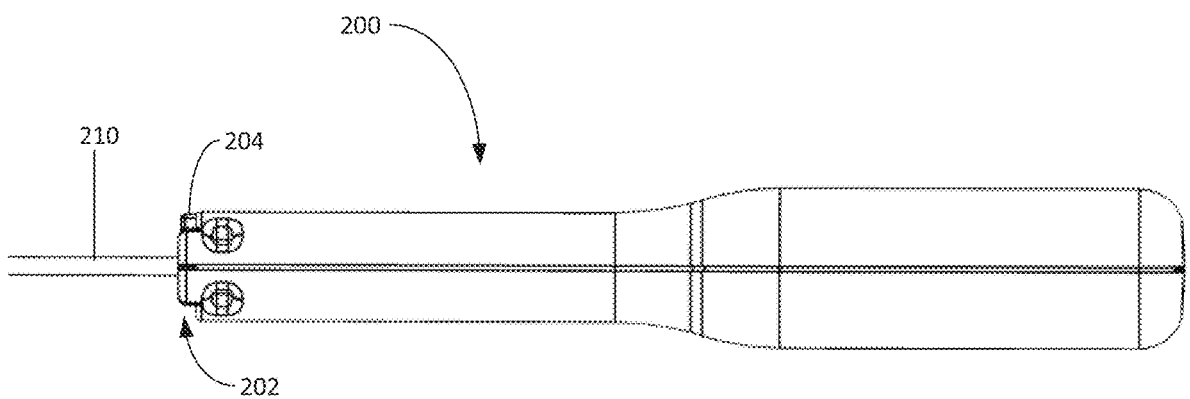
FIG. 6 shows a top view of a handle including a needle

FIG. 6 shows a top view of the handle 200 including the needle 210. As can be seen, the proximal portion of the handle 200 can define a retaining feature 202 that can take the form of a slot having a size and shape corresponding to the protrusion 119 or a portion of the interlock component 100. A feature, such as rib 204, is positioned opposite the retaining feature 202 and adjacent to the needle 210, as described herein.

Figure 7:
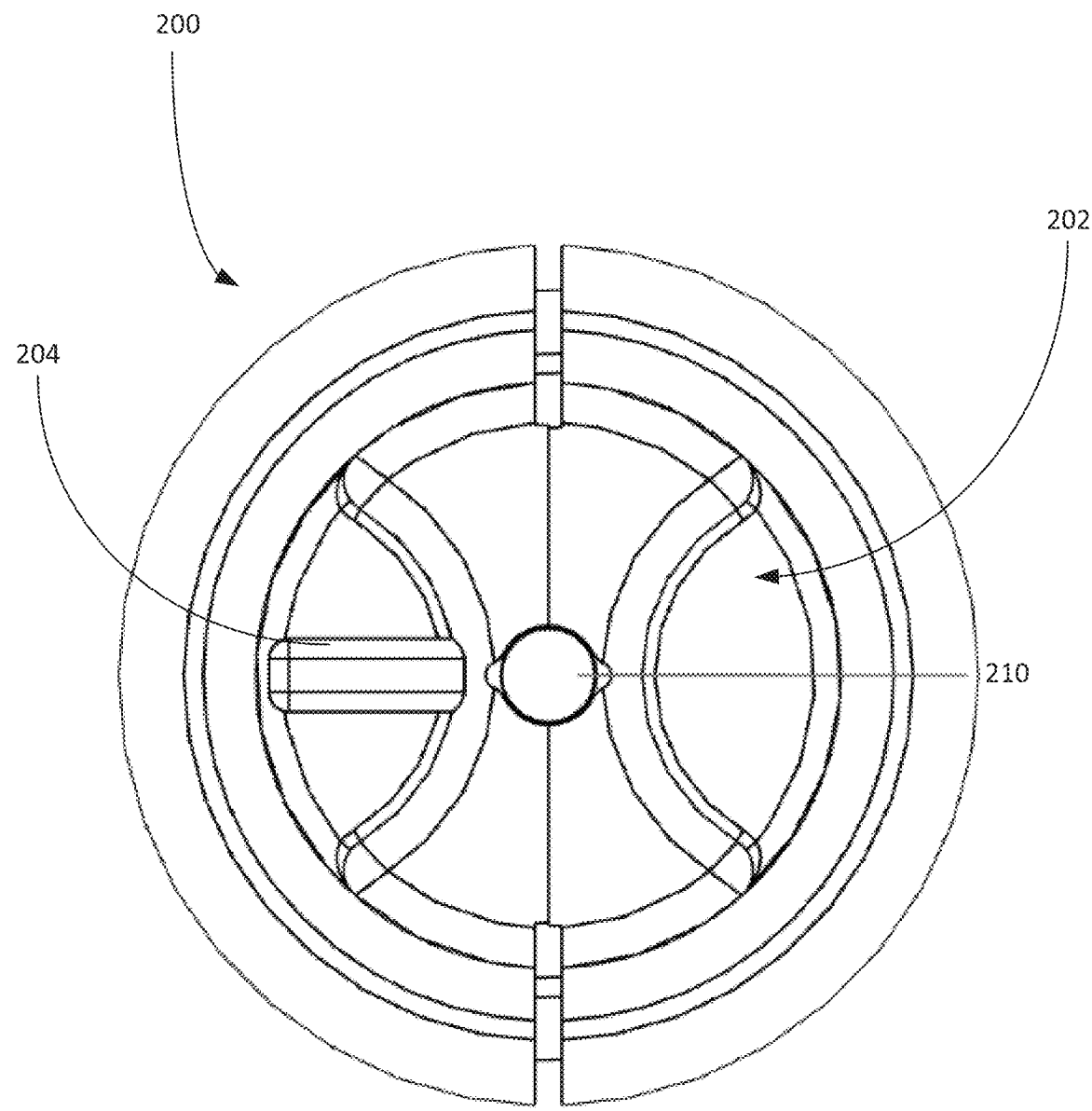
FIG. 7 shows a front view of a handle.

FIG. 7 shows a front view of the proximal portion of the handle 200 including the retaining feature 202 defined by the handle 200 adjacent to the needle 210. In some examples, the portion of the proximal face of the handle 200 opposite the retaining feature 202 can include a similarly shaped and sized feature with a rib 204 protruding therefrom to prevent complete engagement between the interlock component 100 and the handle 200, when not oriented in the desired spatial relationship.

FIG. 8A illustrates a system for fixing a desired spatial relationship between two medical instruments, such as needle 140 and needle 210, including an interlock component 100, as described with respect to FIGS. 1-4, and a handle 200, as described with respect to FIGS. 5-7. As can be seen, the interlock component 100 including the needle 140 have been laterally aligned with the handle 200 and second needle 210 such that the needle 210 is disposed in the slot 116 defined by the head 110 of the interlock component 100. Accordingly, a desired lateral spacing between the needles 14, 210 can be achieved while the offset and angular relationship of each needle in a second direction, for example, relative to a patient or insertion site or one another, can be manipulated prior to fixing the desired spatial relationship.

In some examples, the slot 116 can allow a user to laterally align the interlock component 100 with the needle 210 at any length or position along the needle 210 without the need to pass the entire needle through the slot 116. Further, while the needle 210 is shown disposed in slot 116, the needle 210 can alternatively be disposed in slot 118 if the interlock component is rotated 180 degrees, thereby allowing for multiple positions of the interlock component to achieve the desired spatial relationship. As can also be seen, the protrusion 119 of the interlock component 100 is oriented such that it faces the retaining feature 202 of the handle.

FIG. 8B shows the interlock component 100 as it is being moved or translated towards the handle 200 prior to achieving fixation in the desired spatial relationship. The needle 140, retained by the interlock component 100, has thus also been translated in the same direction and distance as the interlock component. At this point, the magnet positioned in the handle 200 adjacent to the retaining feature 202 can exert an attractive force on one or more of the magnets 132, 134 disposed within the head 110 and adjacent to the rear surface of the protrusion 119. Accordingly, the magnet of the handle can exert a force to pull the interlock component 100 into the desired spatial relationship with the handle 200. During operation, a user can also feel the force exerted by the magnets as the interlock component 100 and handle 200 are moved towards one another, thereby providing a tactile indication that the interlock component 100 and handle are aligned in a manner to achieve the desired spatial relationship.

Further, in some examples, the handle 200 can include a second magnet positioned on the other side of the location where the needle 210 meets the handle 200 that can exert a repulsive force on the magnet or magnets 132, 134 of the interlock component. Accordingly, if the interlock component 100 is moved towards the handle 200 but is not oriented in a manner that will achieve the desired spatial relationship when the interlock component 100 and handle contact one another the user will feel the repulsive force, and thus receive an indication that a realignment of the components may be necessary to achieve the desired spatial relationship. If the user persists with moving the interlock component 100 and handle 200 towards one another despite this repulsive force, the rib 204 can prevent completed mating of the interlock component and handle 200 in this undesired orientation. Further, the rib can provide a visually discernible gap between the protrusion 119 and the proximal surface of the handle 200 to indicate misalignment. When the interlock component 100 and the handle are fixed in the desired spatial relationship, no such gap may be present, thereby providing a visible indicia to the user that the desired spatial relationship has been achieved.

FIG. 8C shows the interlock component and the handle 200, and thus the needle 140 and needle 210, fixed in the desired spatial relationship. The protrusion 119 of the interlock component has engaged and is retained by the retaining feature 202 of the handle, while the magnet 132 of the interlock component 100 and the magnet within the handle 200 exert an attractive force on one another to fix or secure the desired spatial relationship. The engagement of the magnets with one another provides a force to fix the spatial relationship without requiring the additional operation of a component by the user or the addition of further moving parts to the system, thereby simplifying manufacturing and use. In some examples, however, additional features or components, such as a clip, electromechanical feature, and the like, can additionally or alternatively fix the spatial relationship of interlock component 100 and handle 200.

FIG. 9A illustrates a top cross-sectional view of a system for fixing a desired spatial relationship between a needle 140 and a needle 210 including an interlock component 100, as described with respect to FIGS. 1-4, and a handle 200, as described with respect to FIGS. 5-7. The interlock component 100 and the handle 200 are arranged in the same spatial relationship as shown in FIG. 8A. It can be seen in FIG. 9A that magnet 134 of the interlock component 100 is aligned with the magnet 212 of the handle 200 that is configured to exert an attractive force on the magnet 134 when they are brought within a certain distance of one another in the desired alignment. Magnet 214 of the handle 200 is also shown and is configured to exert a repulsive force on either or both of magnets 132, 134 if the interlock component 100 is moved towards the handle 200 in an undesirable alignment, for example, if the interlock component is positioned on the opposite side of needle 210.

Further, as can be seen in FIG. 9A, there is a small portion of material of the interlock component 100 disposed between the magnets 132, 134 and the rear surface of the protrusion 119 to allow for a desired level of attractive force between the magnets 132, 134 and the magnet 212. The magnet 212 can similarly be positioned within the handle such that only a thin region of material is disposed between the magnet 212 and the exterior environment. In some examples, the thickness of the material disposed between a magnet 132, 134 and the exterior environment can be less than about 0.1 inches, for example, less than about 0.05 inches, less than about 0.025 inches, or less than about 0.01 inches, or thinner.

FIG. 9B shows the interlock component 100 and the handle 200 in the same position as illustrated in FIG. 8B. FIG. 9C shows the interlock component 100 and the handle 200 in the same position as illustrated in FIG. 8C and fixed in the desired spatial relationship. Needle 140 and needle 210 are also fixed in the desired spatial relationship with respect to another. As can be seen, movement of the interlock component 100 towards the handle 200 has also resulted in movement of the needle 140 towards the handle 200 relative to the needle 210. The end points of the needles 140, 210 are thus positioned and fixed in the desired spatial relationship, for example, to allow accurate monitoring of an interstitial therapy, as described herein. Accordingly, the desired spatial relationship can include a desired lateral offset between the needles 140, 210, a desired angular offset of the needles 140, 210 relative to one another, as well as a desired depth, or offset along a direction facing the patient or handle 200 relative to one another.

Although certain examples are described herein with respect to particular procedures and medical devices, such as those used in FLA or LITT procedures, the present disclosure applies to any medical devices or instruments where it can be desirable to maintain a spatial relationship therebetween. Accordingly, the methods, systems, and devices described herein can be used for and applied to a broad array of medical devices and procedures and are not limited to those described herein.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not meant to be exhaustive or to limit the embodiments to the precise forms disclosed. It will be apparent to one of ordinary skill in the art that many modifications and variations are possible in view of the above teachings.

What is claimed is:

1. A system for fixing a desired spatial relationship between medical devices, comprising:
   an interlock component including:
   a body defining an aperture to receive and retain a first needle,
   a head connected to the body and defining a slot extending parallel to the aperture;
   a first magnet at least partially surrounded by the head disposed between the aperture and the slot; and
   a handle configured to receive and retain a second needle, the handle defining a retaining feature for receiving a portion of the interlock component and including a second magnet positioned adjacent to the retaining feature;
   wherein the second magnet attracts the first magnet to retain the portion of the interlock component in the retaining feature such that the interlock component is oriented in the desired spatial relationship relative to the handle.

2. The system of claim 1, further comprising a first needle retained by the body and a second needle retained by the handle.

3. The system of claim 2, wherein the desired spatial relationship between the interlock component and the handle corresponds to a desired spatial relationship between the first needle and the second needle.

4. The system of claim 2, wherein the first needle comprises one of a thermal sensor, an optical sensor, or a multimodal sensor.

5. The system of claim 2, wherein the second needle comprises an energy source.

6. The system of claim 2, wherein the first and second magnets comprise rare-earth magnets.

7. The system of claim 1, wherein the body and head comprise polycarbonate.

8. The system of claim 1, wherein a thickness of material between the first magnet and a rear surface of the head is less than 0.01 inches.

9. The system of claim 1, wherein the handle comprises a protrusion disposed opposite the retaining feature to prevent retention of the interlock component by the handle in an undesired spatial relationship.

10. The system of claim 1, wherein the handle comprises a third magnet configured to exert a repulsive force on the first magnet when the interlock component is not oriented in the desired spatial relationship relative to the handle.

11. The system of claim 1, wherein the interlock component is rotatable with respect to the handle when the second needle is disposed in the slot and the portion of the interlock component is not received by the retaining feature.

12. The system of claim 1, wherein the desired spatial relationship includes a desired angle and spatial offset between the interlock component and the handle.

13. The system of claim 1, wherein the system further comprises a visible indicia that the interlock component and handle are in the desired spatial relationship.

14. The system of claim 1, wherein the portion of the interlock component comprises a protrusion and the retaining feature comprises a portion of the handle defining a slot having a size and shape corresponding to the protrusion.

* * * * *